United States Patent [19]
Gardiner

[11] 4,228,796
[45] Oct. 21, 1980

[54] INSULIN INJECTION GUIDE

[76] Inventor: Marie A. Gardiner, 1 Holly Rd., Stratford, N.J. 08084

[21] Appl. No.: 22,086

[22] Filed: Mar. 19, 1979

[51] Int. Cl.³ ............................................. A61M 5/00
[52] U.S. Cl. ..................................................... 128/215
[58] Field of Search ............... 128/215, 213 R, 218 R, 128/92 EB

[56] References Cited

U.S. PATENT DOCUMENTS

| | | | |
|---|---|---|---|
| 2,245,350 | 6/1941 | Marshall | 128/215 X |
| 3,542,022 | 11/1970 | Bartnik | 128/215 |
| 3,547,121 | 12/1970 | Cherry | 128/215 |

*Primary Examiner*—John D. Yasko
*Attorney, Agent, or Firm*—Duffield & Lehrer

[57] ABSTRACT

A flexible sheet-like material has fifteen holes therethrough which are consecutively numbered one to fifteen on one side thereof and sixteen to thirty on the other. A pair of straps including Velcro attachments are adapted to support the guide on the right thigh with the numbers one to fifteen exposed or on the left thigh exposing the numbers sixteen to thirty. The user can then inject himself through the hole having the same number as the day of the month. In a modified form of the invention, there are seven holes which are identified by the days of the week on each side thereof. When using this embodiment, the user injects himself through the hole corresponding to the proper day of the week. Several pockets formed in the sheet material may be used for storing the syringe and a supply of insulin.

9 Claims, 5 Drawing Figures

U.S. Patent  Oct. 21, 1980  4,228,796
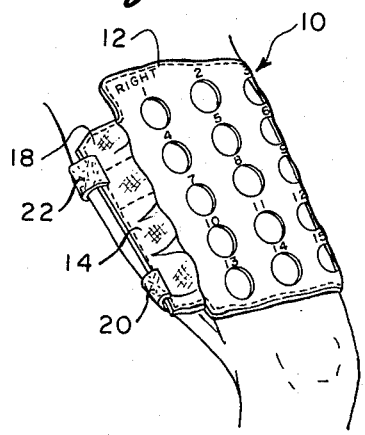
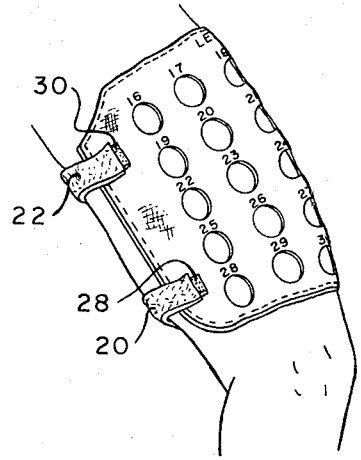
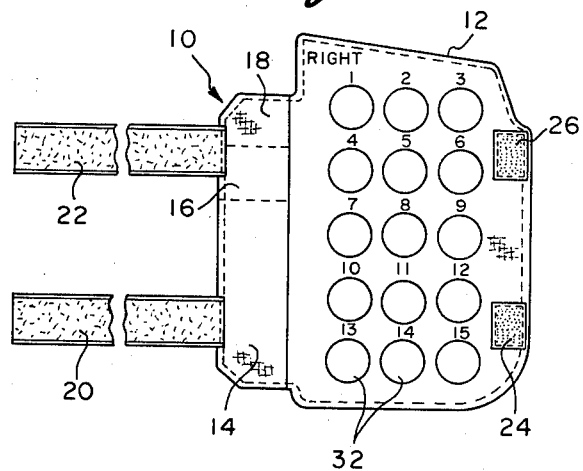
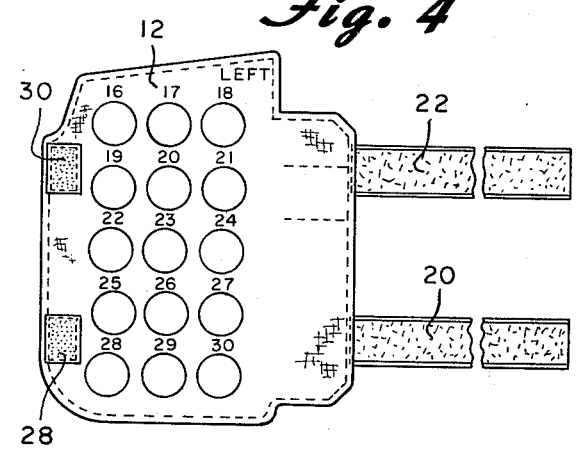
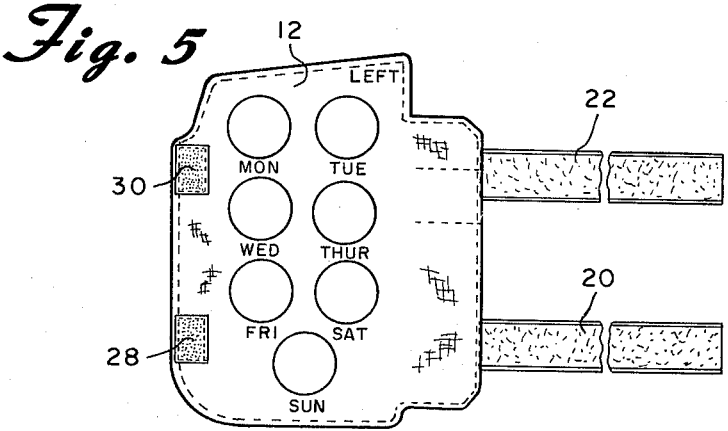

INSULIN INJECTION GUIDE

BACKGROUND OF THE INVENTION

The present invention is directed toward an insulin injection guide and more particularly toward a device which is adapted to be placed around a person's thigh to assist him in giving himself an insulin injection in the proper location.

Diabetes mellitus is a disease or disorder which is unfortunately shared by many people both young and old. The condition is characterized by an inadequate secretion or utilization of insulin which results in excessive amounts of sugar in the blood. In many cases, the condition can be controlled by observing a strict diet. Other, more serious cases, can only be controlled by regular injections of insulin.

Since an insulin injection must be received daily, it is impractical to so frequently visit a doctor or nurse and accordingly most people who must take insulin injections are taught to administer the injections themselves. In recent years, even relatively young children have been taught to administer their own insulin injections.

Insulin injections are normally given in the front portion of a person's thigh. This is done for both physiological reasons and for convenience since one cannot only see what they are doing but can utilize two hands during the injection process. In addition, since various adverse conditions can result by repeatedly injecting oneself in the same position, users of insulin are taught to inject themselves in a different spot on the thigh each day and to utilize both their right and left thighs. Unfortunately, many people and particularly the very young and the very old may forget where they gave themselves the last injection or may merely forget to vary the injection sight and may tend to continually give themselves injections in the same location.

SUMMARY OF THE INVENTION

The present invention avoids the above problems by providing a guide for informing an insulin user as to where to administer an injection. The guide is comprised of a flexible sheet-like material which has fifteen holes passing therethrough which are consecutively numbered one to fifteen on one side and sixteen to thirty on the other. A pair of straps including Velcro attachments are adapted to support the guide on the right thigh with the numbers one to fifteen exposed or on the left thigh exposing the numbers sixteen to thirty. The user can then inject himself through the hole having the same number as the day of the month. In a modified form of the invention, there are seven holes which are identified by the days of the week on each side thereof. When using this embodiment, the user injects himself through the hole corresponding to the proper day of the week. Several pockets formed in the sheet material may be used for storing the syringe and a supply of insulin.

BRIEF DESCRIPTION OF THE DRAWINGS

For the purpose of illustrating the invention, there are shown in the accompanying drawings forms which are presently preferred; it being understood that the invention is not intended to be limited to the precise arrangements and instrumentalities shown.

FIG. 1 is a perspective view of an insulin injection guide constructed in accordance with the principles of the present invention and being utilized on a person's right thigh;

FIG. 2 is a view similar to FIG. 1 showing the device being utilized on a person's left thigh;

FIG. 3 is a front plan view of the device shown in FIG. 1;

FIG. 4 is a view similar to FIG. 3 showing the reverse side of the guide, and

FIG. 5 is a plan view of a modified form of an insulin injection guide.

DETAILED DESCRIPTION OF THE PREFERRED EMBODIMENT

Referring now to the drawings in detail wherein like reference numerals have been used throughout the various figures to designate like elements, there is shown in FIGS. 1-4 a first embodiment of an insulin injection guide constructed in accordance with the principles of the present invention and designated generally as 10.

Guide 10 is comprised of a body portion 12 which is made from a substantially flexible and flat sheet-like material of generally rectangular shape. A plurality of pockets 14, 16 and 18 are formed in the body portion 12 adjacent one edge thereof. Pocket 14 is constructed so as to be sufficiently large to store one or more syringes therein. Vials of insulin may be stored in pockets 16 and 18.

Secured to one edge of the body portion 12 are a pair of straps 20 and 22. These straps 20 and 22 are covered on both sides thereof with a felt-like material which forms one half of a connecting means commonly known as Velcro. The other half of the Velcro connectors which are a plurality of small hooks mounted on support pads are attached to the other edge of the body portion 12 in line with the straps 20 and 22. Velcro pads 24 and 26 are located on one surface of the body portion 12 and pads 28 and 30 are attached to the reverse side of the body portion 12 directly behind pads 24 and 26, respectively. As a result, and as can be seen in FIGS. 1 and 2, the straps 20 and 22 can be moved either forwardly or rearwardly to attach to the pads 24 and 26 or 28 and 30 so that the device can be mounted about a person's thigh with either the front surface of the body portion 12 exposed and the rear surface against the person's leg or the rear surface exposed and the front portion against the person's leg.

The body portion 12 of the guide 10 has a plurality of holes 32 passing therethrough which may be numbered or otherwise identified on the surface of the guide 10 so as to assist the user in selecting the proper hole for administering an injection. For example, if there are ten holes numbered consecutively one to ten and the user gave himself an injection in hole number three yesterday then he will inject through hole number four today. Preferably, one side of the guide is also identified as "right" and the other side is identified as "left". This, of course, indicates that the right side is to be exposed when the device is used on the right leg and the left side is to be exposed when it is used on the left leg.

The use of the insulin injection guide 10 should be readily apparent. The device is placed with the body portion 12 over the forward part of a person's thigh and the straps 20 and 22 are wrapped around the person's leg and are secured to the pads 24 and 26 or 28 and 30. While the guide 10 may not be placed on the user's leg in the exact position each time it is utilized, the user will find that he positions the same in substantially the same position each time the device is used. Furthermore, exact positioning of the guide 10 is not absolutely necessary. After the guide 10 is placed on the leg, the proper hole is selected and the user administers an injection to his thigh through the selected hole. The holes 32 are sufficiently large so that even a person with a relatively unsteady hand can pass a needle therethrough without the same coming into contact with the body portion 12 itself. This avoids contamination of the needle and possible infection. In addition, the entire guide 10 is preferably comprised of a material or is coated with a material which can be easily and thoroughly cleaned.

While the exact number of holes 32 and the specific numbers or other indicia associated therewith are not critical to the operation of the present invention, there are several systems which are definitely preferred. For example, if there are fifteen holes, these may be consecutively numbered one to fifteen on the right side of the body portion 12 and may be numbered sixteen to thirty on the left side thereof. These numbers would then correspond to the days of the month which means that the user of the device need not have to remember the number which he used yesterday. All that is necessary is that they look at a calendar or recall the present day of the month and they will know through which hole they should be giving themselves an injection. For example, if it is the seventeenth day of the month then they will locate hole number seventeen which is found on the left side of the device. The device is then positioned on the left thigh and an injection may be given through hole seventeen. Since there are several months which have thirty-one days, an additional hole numbered thirty-one may be added to the device or the user may simply give himself an injection on the thirty first day through substantially any one of the other holes.

It should be readily apparent that it is not absolutely necessary to number the holes consecutively. For example, it might be possible to have all of the odd numbered holes on the right side and all of the even numbered holes on the left. In this way, injections would be given on the right thigh on odd numbered days and on the left thigh on even numbered days. Furthermore, it is possible to have less than fifteen holes with each hole having more than one number or other indicia associated therewith. For example, there may be eight holes with the holes on the right side being marked 1/17, 2/18, 3/19 etc. and the holes on the left side being marked 9/25, 10/26, 11/27 etc.

Another embodiment of the insulin injection guide is shown in FIG. 5. In this embodiment, there are seven holes which are marked with the days of the week i.e. Sunday through Saturday. Preferably, both sides of the device carry the same indicia. Using this device, one need only know the day of the week and remember whether he should be injecting into his right or left thigh. This embodiment may be preferable for smaller children since with fewer holes the entire device can be made somewhat smaller. It must be kept in mind that the holes themselves cannot be too small or there becomes too great a chance that the tip of the needle may contact the body portion 12 of the guide and become contaminated.

The present invention may be embodied in other specific forms without departing from the spirit or essential attributes thereof and accordingly, reference should be made to the appended claims rather than to the foregoing specification as indicating the scope of the invention.

I claim:

1. An injection guide comprising:
   a substantially flexible sheet-like material of predetermined shape, said material having a plurality of holes passing therethrough;
   means attached to said material for securing the same to a person's thigh; and
   means associated with each of said holes for identifying each hole and for distinguishing each hole from each of the other holes, said means associated with each of said holes being indicia means identifying the days of the week.

2. An injection guide as claimed in claim 1 wherein said plurality of holes comprises seven holes.

3. An injection guide as claimed in claim 1 wherein said securing means are straps.

4. An injection guide comprising:
   a substantially flexible sheet-like material of predetermined shape, said material having a plurality of holes passing therethrough;
   means attached to said material for securing the same to a person's thigh; and
   means associated with each of said holes for identifying each hole and for distinguishing each hole from each of the other holes, said means associated with each of said holes being indicia means in the form of numbers identifying the days of the month.

5. An injection guide as claimed in claim 4 wherein said securing means are straps.

6. An injection guide as claimed in claim 4 wherein said sheet-like material has first and second surfaces and wherein said securing means is adapted to selectively secure the guide to a person's thigh with either of said surfaces exposed.

7. An injection guide as claimed in claim 6 wherein there are fifteen holes, said holes being identified by the numbers one to fifteen, respectively, on said first surface and sixteen to thirty, respectively, on said second surface.

8. An injection guide comprising:
   a substantially flexible sheet-like material of predetermined shape, said material having a plurality of holes passing therethrough;
   means attached to said material for securing the same to a person's thigh;
   means associated with each of said holes for identifying each hole and for distinguishing each hole from each of the other holes, and
   at least one pocket formed in said material for holding injection supplies.

9. An injection guide as claimed in claim 8 wherein said securing means are straps.

* * * * *